United States Patent
Haytman et al.

(10) Patent No.: US 8,574,490 B2
(45) Date of Patent: Nov. 5, 2013

(54) METHODS AND APPARATUS FOR REDUCING COUNT OF INFECTIOUS AGENTS IN INTRAVENOUS ACCESS SYSTEMS

(75) Inventors: Eyal Haytman, Kfar Vradim (IL); Assaf Deutsch, Tzafaríya (IL); Eliahu Pewzner, Modi'in Ilit (IL)

(73) Assignee: Bactriblue, Ltd., Holon (IL)

( * ) Notice: Subject to any disclaimer, the term of this patent is extended or adjusted under 35 U.S.C. 154(b) by 447 days.

(21) Appl. No.: 12/751,365

(22) Filed: Mar. 31, 2010

(65) Prior Publication Data

US 2011/0085936 A1    Apr. 14, 2011

Related U.S. Application Data

(60) Provisional application No. 61/165,365, filed on Mar. 31, 2009.

(51) Int. Cl.
| | |
|---|---|
| *A61L 2/00* | (2006.01) |
| *A61F 5/00* | (2006.01) |
| *A61M 5/32* | (2006.01) |
| *A61N 5/00* | (2006.01) |

(52) U.S. Cl.
USPC ............... 422/24; 422/22; 422/23; 600/133; 600/467; 602/2; 604/264; 604/265; 250/492.1

(58) Field of Classification Search
None
See application file for complete search history.

(56) References Cited

U.S. PATENT DOCUMENTS

| | | | |
|---|---|---|---|
| 3,986,508 A | 10/1976 | Barrington | |
| 4,276,256 A | 6/1981 | Karamian | |
| 4,340,148 A | 7/1982 | Beckham | |
| 4,342,915 A | 8/1982 | Karamian | |
| 4,412,834 A | 11/1983 | Kulin | |
| 4,503,333 A | 3/1985 | Kulin et al. | |
| 4,566,480 A | 1/1986 | Parham | |
| 5,260,020 A | 11/1993 | Wilk et al. | |
| 5,279,557 A | 1/1994 | Lomick | |
| 6,461,568 B1 | 10/2002 | Eckhardt | |
| 6,551,346 B2 | 4/2003 | Crossley | |

(Continued)

FOREIGN PATENT DOCUMENTS

| | | |
|---|---|---|
| WO | 9502324 A1 | 1/1995 |
| WO | 2004014487 A1 | 2/2004 |
| WO | 2008066943 A2 | 6/2008 |

OTHER PUBLICATIONS

Written Opinion of the International Searching Authority, mailed Aug. 10, 2011 in International Application No. PCT/IL11/00244.

(Continued)

*Primary Examiner* — Neil N Turk
(74) *Attorney, Agent, or Firm* — Ostrager Chong Flaherty & Broitman P.C.

(57) ABSTRACT

Methods and apparatus for preventing patient bloodstream infection by microorganisms during administration of various medications or fluids through IV lines. In particular, the invention reduces contamination of IV lines, connecters, stopcock valves, manifolds, ports, etc. by means of irradiation by violet and/or blue light. Each embodiment comprises a source of violet and/or blue light and an optical element optically coupled to that light source for shaping the radiation pattern of the light emitted by the light source. Preferably, a light-emitting diode or a laser diode that emits light in the desired wavelength can be used. The optical element, optically coupled to the light source, is embedded or installed in or attached to a component of an IV set, the emitted light being directed to a "point of entry" or any other stagnation point of an IV set.

16 Claims, 16 Drawing Sheets

(56) References Cited

U.S. PATENT DOCUMENTS

| | | |
|---|---|---|
| 2003/0031586 A1 | 2/2003 | Eckhardt |
| 2004/0092890 A1 | 5/2004 | Ash |
| 2006/0216193 A1 | 9/2006 | Johnson |
| 2008/0027399 A1 | 1/2008 | Harding |
| 2008/0051736 A1 | 2/2008 | Rioux |
| 2008/0104978 A1 | 5/2008 | Kim |
| 2009/0130169 A1 | 5/2009 | Bernstein |

OTHER PUBLICATIONS

Elman et al., Abstract of: The effective treatment of acne vulgaris by a high-intensity, narrow band 405-420 nm light source, Journal of Cosmetic and Laser Therapy, vol. 5, Issue 2, pp. 111-117 (2003).

Raad et al., Ultrastructural Analysis of Indwelling Vascular Catheters: A Quantitative Relationship between Luminal Colonization and Duration of Placement, The Journal of Infectious Diseases; 168:400-7 (1993).

Raad, Intravascular-catheter-related infections, The Lancet, vol. 351, 893-98 (1998).

Mermel, New Technologies to Prevent Intravascular Catheter-Related Bloodstream Infections, Emerging Infectious Diseases, vol. 7, No. 2, pp. 197-199 (2001).

Guffey et al., Effects of Combined 405-nm and 880-nm Light on *Staphylococcus aureus* and *Pseudomonas aeruginosa* in Vitro,Photomedicine and Laser Surgery, vol. 24, No. 6, pp. 680-683 (2006).

Fukui et al., Specific-wavelength visible light irradiation inhibits bacterial growth of *Porphyromonas gingivalis*, Journal of Periodontal Research, vol. 43, pp. 174-178 (2008).

Enwemeka et al., Visible 405 nm SLD Light Photo-Destroys Methicillin-Resistant *Staphylococcus aureus* (MRSA) In Vitro, Laser in Surgery and Medicine, 40:734-747 (2008).

Elliott et al., Novel Approach to Investigate a Source of Microbial Contamination of Central Venous Catheters, Eur. J. Clin Microbiol. Infect. Dis., vol. 16, No. 3, pp. 210-213 (1997).

SwabCap Luer Access Valve Disinfection Cap, Excelsior Medical Corporation, www.excelsiormedical.com/swabcap.php.

Baxter U.S.-Healthcare Professionals, V-Link Luer-Activated Device with VITALSHIELD Protective Coating, www.baxter.com/healthcare_professionals/products/vlink.html.

Guffey et al., In Vitro Bactericidal Effects of 405-nm and 470-nm Blue Light, Photomedicine and Laser Surgery, vol. 24, No. 6, pp. 684-688 (2006).

Elcam Medical Inc., www.devicelink.com/company98/co/171/17118.html.

Peterson, Central Line Sepsis, Clinical Journal of Oncology Nursing, vol. 7, No. 2, pp. 218-221 (2003).

Elcam Medical, B-Stop Whitepaper, Rev. 5, May (2007).

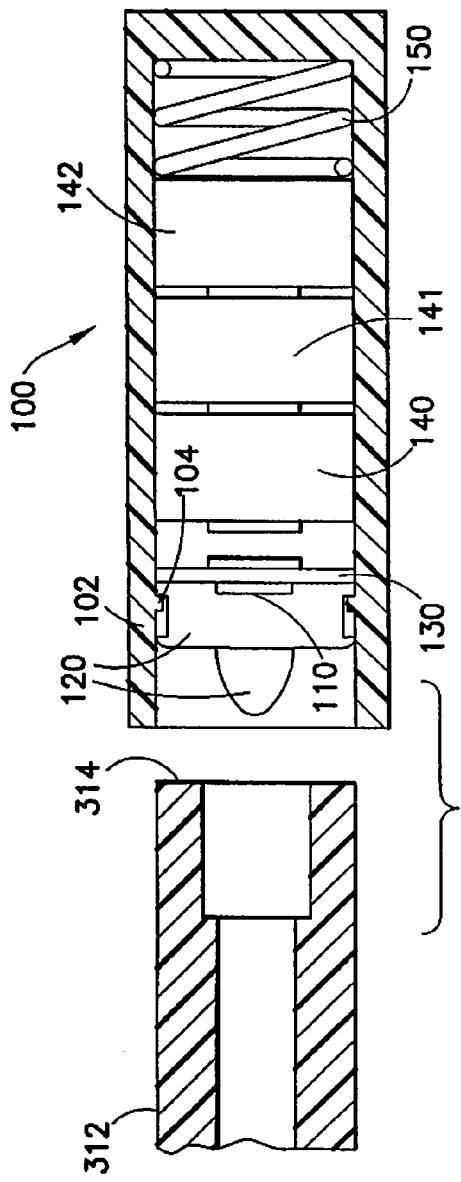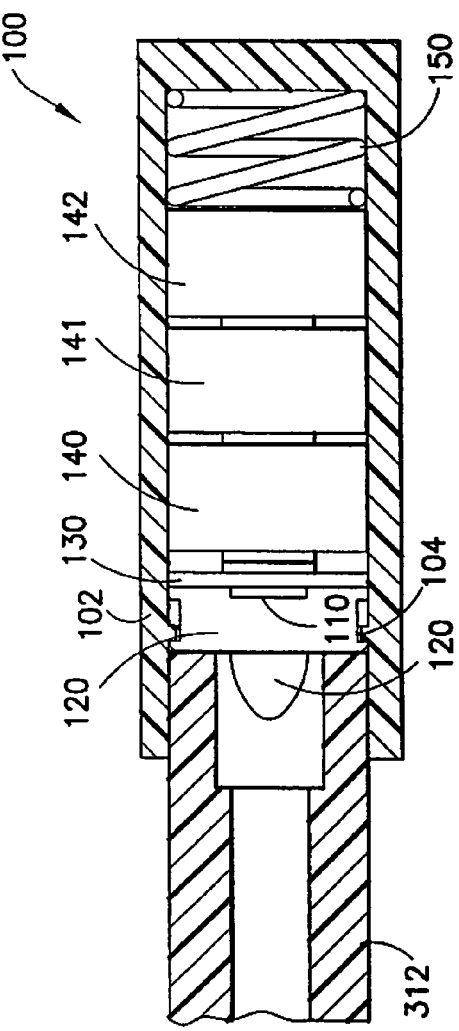

METHODS AND APPARATUS FOR REDUCING COUNT OF INFECTIOUS AGENTS IN INTRAVENOUS ACCESS SYSTEMS

RELATED PATENT APPLICATION

This application claims the benefit, under Title 35, United States Code, §119(e), of U.S. Provisional Application No. 61/165,365 filed on Mar. 31, 2009.

BACKGROUND

This invention generally relates to methods and systems for reducing the risk of patient bloodstream infection by microorganisms during administration of various medications and fluids through lines. In particular, the invention relates to methods and systems for reducing the count of infectious agents and inhibiting the growth of microorganisms inside intravenous (IV) lines and accompanying connectors, stopcock valves, ports and tubes.

It is a common practice in medicine to administer various medications and fluids into and withdraw blood from a patient's vascular system. For these purpose, various intravenous access devices exist. Such a device typically has a hollow needle, the tip of which is inserted into a patient's blood vessel for variable periods of time—from seconds (for example, injections and blood sampling) to years (for example, total parenteral nutrition, chemo-therapy and dialysis). All such devices bypass several natural anti-infection defense barriers and introduce a risk of direct bloodstream contamination. The general terms for these devices is "lines." The type of infection that arises from the use of such "lines" is called "line sepsis." Elaborate and complicated precautions and prevention techniques are in use, and include use of one or more of the following means: sterile equipment, sterile insertion technique, aseptic handling techniques, replacement of the "lines" as indicated by various protocols, antibiotics, and antibacterial substances impregnated into catheters.

One of the unsolved problems that is especially relevant to intravascular catheters with longer time of use is colonization by microorganisms of the catheter itself and its associated connectors, stopcocks, ports, valves and tubes. The methods of cleaning and disinfecting indwelling catheters and associated tubes, valves and connectors are of low efficacy, and for that reason, in cases of suspected contamination the components are preferably replaced or removed. Decontamination of indwelling devices and associated valves, ports, connectors and tubing is very problematic because the patient, his blood, and the administered medicine are potentially exposed to all of the physical, chemical and pharmacological effects of such decontamination.

One currently available method of keeping the line components, such as stopcock valves, free of microbiological contamination uses silver ions embedded in the stopcock device. Products such as Elcam Medical Inc.'s antimicrobial stopcocks provide two layers of protection: (i) a closed system designed to prevent contaminants' penetration into the stopcock fluid path and thereby reduce the risk of bloodstream infections; and (ii) silver ions to reduce and prevent bacteria colonization on the product.

The disadvantages of using silver ions and chlorhexidine technology are the following: (a) It starts to act only after the polymer with embedded silver ions is in a wet condition and is active for a minimum of 6-8 hours, while during that time microorganisms already start to grow and multiply. (b) It relies on disinfection materials that are present only in the area close to the flow path walls and that wash away when the line is flushed. (c) The quantity of disinfection material that is effective is declining as time passes, whereas the risk of contamination rises as time passes. (d) The technology is limited only to polymers that can be impregnated or applied as a coating.

Another known method for sterilizing the connection junctions of tubing connecting a catheter to a solution container is to expose the connection junctions to ultraviolet radiation. For example, U.S. Pat. No. 4,412,834 discloses antimicrobial ultraviolet irradiation of connectors for continuous ambulatory peritoneal dialysis.

There is a need for improved apparatus and improved methods for reducing the risk of patient bloodstream infection by microorganisms during administration of various medications and fluids through lines and during the withdrawal of blood samples. This need is especially great at those sites in intravenous access systems where stagnation occurs.

BRIEF SUMMARY

The present invention is directed to methods, systems and devices for reducing catheter-related bloodstream infections. The technology starts fighting the bacteria immediately, at "points of entry" or any other stagnation point of an IV set. A variety of devices can be designed to meet the standard features of conventional IV sets such as Luer connectors or unique features according to the market need.

One object of the invention is to stop bacteria proliferation at an early stage. A series of devices can be developed that can be used to treat different stagnation locations from the proximal side of the IV set, such as an IV bag connection, all the way to the catheter hub. In accordance with some embodiments, sets of devices, e.g., caps, can be fitted onto points of entry of the IV sets, such as the standard ISO 594 Luer connectors.

Recent photobiology research has shown that various types of microorganisms can be eradicated by irradiation with visible light, especially in the "violet/blue spectral region." As used herein, the term "violet/blue spectral region" refers to blue light comprising wavelengths in the range of 455-492 nm and violet light comprising wavelengths in the range of 390-455 nm, consistent with the definitions of "blue" and "violet" given in the Academic Press Dictionary of Science and Technology, Harcourt Brace Jovanovich, New York (1992). The various bactericidal devices disclosed herein each comprise a light source that preferably emits light having wavelengths in the violet/blue spectral region.

The apparatus and methods disclosed herein can prevent patient bloodstream infection by microorganisms during administration of various medications or fluids through IV lines. In particular, the invention reduces contamination of IV lines, connecters, stopcocks, valves, ports, manifolds, etc. by means of irradiation by violet and/or blue light. Each of the embodiments disclosed herein comprises a source of violet and/or blue light and an optical element optically coupled to that light source for shaping the radiation pattern of the light emitted by the light source. The optical element, optically coupled to the light source, is embedded or installed in or attached to a component of an IV set, the emitted light being directed to a "point of entry" or any other stagnation point of an IV set. Preferably, a light-emitting diode or a laser diode that emits light in the desired wavelength (i.e., in the violet/blue spectral region) can be used.

One aspect of the invention is a method for reducing the count of infectious agents inside an intravenous access system, comprising the following steps: (a) placing an optical element in or on a first portion of an intravenous access system, the optical element being capable of transmitting light and being placed so that any transmitted light will be directed toward a second portion of the intravenous access system; (b) optically coupling the optical element to a source of light; and (c) causing the light source to emit light, the emitted light being transmitted by the optical element toward the second portion of the intravenous access system, wherein the emitted light has a bactericidal effect.

Another aspect of the invention is a system for reducing the count of infectious agents in an intravenous access system, comprising: an optical element that is capable of transmitting light in or on a first portion of an intravenous access system, the optical element being placed so that transmitted light will be directed toward a second portion of the intravenous access system; and a source of light optically coupled to the optical element, wherein the light source emits light, the emitted light being transmitted by the optical element toward the second portion of the intravenous access system, wherein the emitted light has a bactericidal effect.

A further aspect of the invention is a system comprising a tube, a connector having a port at one end and having another end that is in flow communication with the tube at an intersection therewith, and a cap installed on the one end of the connector to close the port or installed on an adapter that is installed on the one end of the connector, the cap comprising a cap housing, a source of light and an optical element that is optically coupled to the light source, the light source and the optical element being disposed inside the cap housing, and the optical element being capable of transmitting light emitted by the light source toward the intersection, wherein the transmitted light has a bactericidal property.

Other aspects of the invention are disclosed and claimed below.

BRIEF DESCRIPTION OF THE DRAWINGS

FIGS. 18 and 19 are drawings showing sectional views of a disposable light-emitting cap in accordance with the seventh embodiment, wherein the light source is activated when the cap is installed on an end of a connector. FIG. 18 shows the device in an OFF state, while FIG. 19 shows the device in an ON state.

Reference will now be made to the drawings in which similar elements in different drawings bear the same reference numerals.

DETAILED DESCRIPTION

Figure 1:
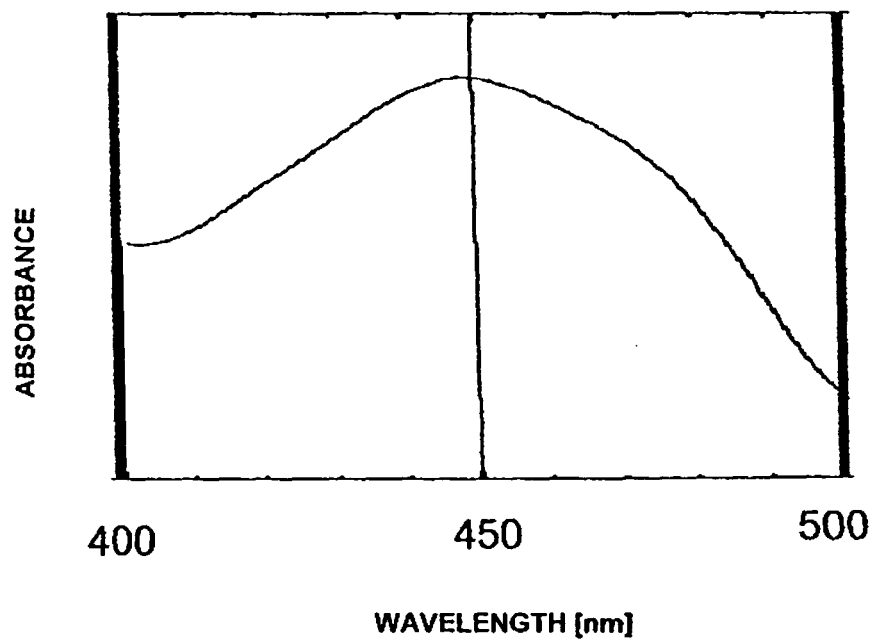
FIG. 1 is a graph showing a typical absorption band of flavin-adenine dinucleotide (FAD).

Recent photobiology research has showed that various types of microorganisms can be eradicated by irradiation of visible light, especially light in the violet/blue spectral region. The photo-contamination reduction effect has been shown for both in vivo and in vitro setups.

Elman et al. [see Elman, M., et al., "The effective treatment of acne vulgaris by a high-intensity, narrow band 405-420 nm light source," J. Cosmetic and Laser Therapy, 5(2), pp. 111-117 (June 2003)] applied narrow-band light at 405-420 nm for treatment of acne vulgaris. Recently the FDA approved narrow-band, high-intensity light therapy for treating acne. Light works by killing the acne-causing bacteria, *P. acnes*, and is being used to treat inflammatory *acne vulgaris* that has not responded to other acne therapies. Current light products do not contain ultraviolet (UV) light, which was a staple of former light therapy used to treat acne. UV light can damage skin and is no longer used to treat acne.

Enwemeka et al. [see Enwemeka, C. S., Williams, D., Hollosi, S., Yens, D., and Enwemeka, S. K., "Visible 405 nm SLD light photo-destroys methicillin-resistant *Staphylococcus aureus* (MRSA) in vitro," Lasers Surg. Med., 40(10), pp. 734-737 (December 2008)] studied the photo-sterilization effect of light at 405 nm on methicillin-resistant *Staphylococcus aureus* (MRSA) in vitro. According to Enwemeka et al., maximum eradication of the US-300 (92.1%) and the IS-853 colonies (93.5%) was achieved within 9.2 and 8.4 minutes of exposure, respectively. According to the authors, the effect was non-linear as increases of energy densities between 1.0 and 15 J/cm$^2$ resulted in more bacteria death than similar increases between 15 and 60 J/cm$^2$.

Fukui et al. [see Fukui, M., Yoshioka, M., Satomura, K., Nakanishi, H., and Nagayama, M., "Specific-wavelength visible light irradiation inhibits bacterial growth of *Porphyromonas gingivalis*," J. Periodontal Res., 43(2), pp. 174-178 (April 2008)] showed that the growth of *Porphyromonas gingivalis* bacteria irradiated at 400 and 410 nm was significantly suppressed compared with a nonirradiated control, whereas wavelengths of 430 nm and longer produced no significant inhibition. A constant energy density of 15 J/cm$^2$ was found to be enough to show an inhibitory effect. Significant inhibition of bacterial growth was found after only 1 min at 50 mW/cm$^2$ irradiation.

Guffey at al. [see Guffey, J. S., and Wilbom, J., "In vitro bactericidal effects of 405-nm and 470-nm blue light," Photomed. Laser Surg., 24(6), pp. 684-688 (December 2006)] showed that both 405-nm and 470-nm irradiation have a bactericidal effect on *Staphylococcus aureus* and *Pseudomonas aeruginosa* bacteria in vitro. The 405-nm light produced a dose-dependent bactericidal effect on Pseudomonas aeruginosa and Staphylococcus aureus (p<0.05), achieving a kill rate of 95.1% and nearly 90%, respectively. The 470-nm light effectively killed *Pseudomonas aeruginosa* at all dose levels, but only killed *Staphylococcus aureus* at 10 and 15 J/cm$^2$. With this wavelength, as much as 96.5% and 62% reduction of *Pseudomonas aeruginosa* and *Staphylococcus aureus* was achieved, respectively. Neither of the two wavelengths proved to be bactericidal with respect to anaerobic *Propionibacterim acnes*.

Guffey et al. [see Guffey, J. S., and Wilbom, J., "Effects of combined 405-nm and 880-nm light on *Staphylococcus aureus* and *Pseudomonas aeruginosa* in vitro," Photomed. Laser Surg., 24(6), pp. 680-683 (December 2006)] showed that combined irradiation of *Staphylococcus aureus* by 405 and 800 nm has a bactericidal effect.

The mechanisms involved in the photo-contamination reduction effect of blue/violet light are still a subject for numerous research efforts. The violet light in the 400-420 nm wavelength range interacts with the Soret absorption band of porphyrins. The higher wavelength blue light around 440-480 nm interacts with absorption band of flavins and riboflavine. The longer wavelength white light and near infra-red (NIR) light interact with cytochromes and higher absorption bands of porphyrins. The absorbed light excites these photosensitizers while subsequent relaxation from the excited state occurs by transferring electrons to O$_2$, thereby generating reactive oxygen species (ROS). When the ROS reach some increased value, they destroy the cell. The phenomenon is known as phototoxicity.

The present invention enables the provision of systems and methods for continuous (during use) contamination reduction of intravascular catheters, tubing, manifolds, stopcocks, valves, ports and connectors. The various embodiments of the invention are designed to illuminate these devices with light of wavelengths 390-492 nm emitted by low-cost light sources such as light-emitting diodes (LEDs) or laser diodes.

As used herein, the terms "light-emitting diode" and "laser diode" refer to devices comprising a semiconductor diode and an optical element optically coupled to that diode for shaping the radiation pattern of the light emitted by the diode. As used herein, the terms "light-emitting diode assembly" (or "LED assembly") and "laser diode assembly" refer to assemblies comprising a printed circuit board (PCB) and either an LED or a laser diode mounted on a surface of that PCB.

Figure 2:
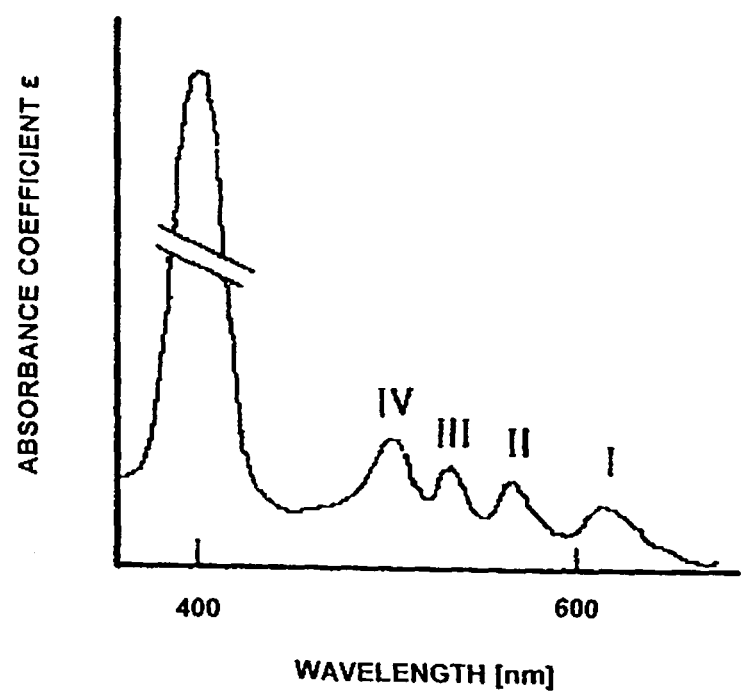
FIG. 2 is a graph showing a typical absorption band of porphyrins.
Figure 3:
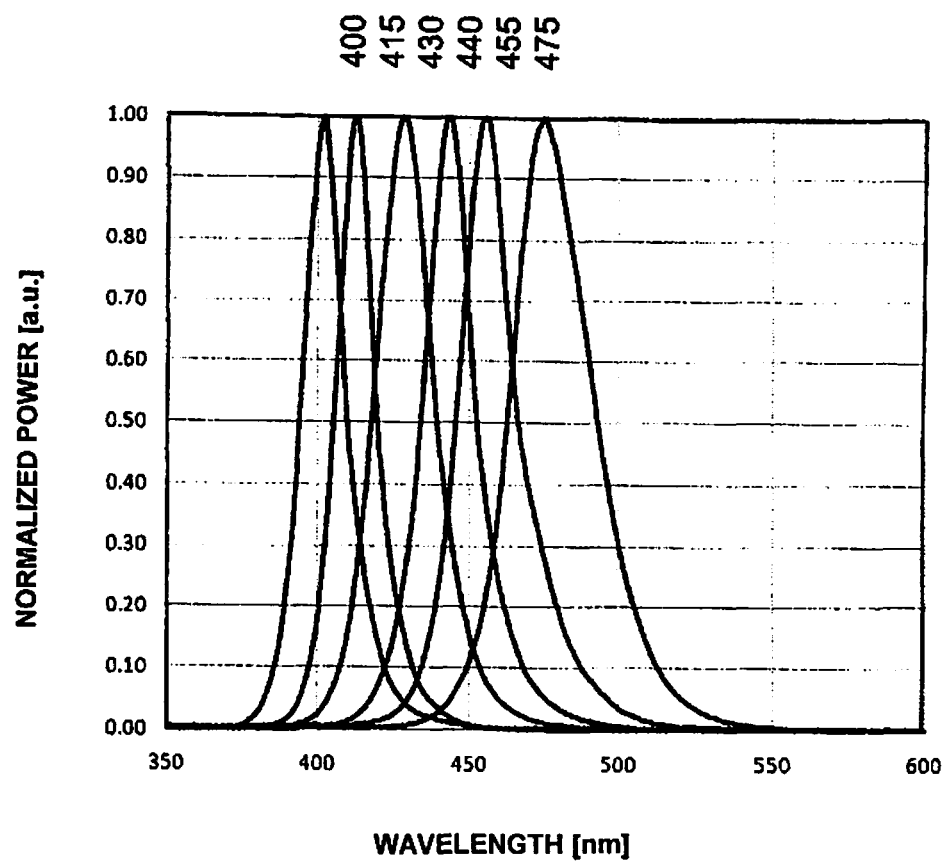
FIG. 3 is a graph showing the emission bands of commercially available high-power LEDs.

The absorption band of flavins [i.e., flavin-adenine dinucleotide (FAD)] is shown in FIG. 1. It is a relatively wide band at 450 nm with a full width at half maximum (FWHM) of about 100 nm. The typical absorption band of porphyrins is shown in FIG. 2. The absorption band for porphyrins comprises a very high Soret absorption band at about 400-410 nm and several smaller absorption Q-Bands (I-IV) along the visible and red parts of the spectrum. FIG. 3 shows the emission bands of commercially available high-power blue and violet LEDs. These LEDs are available from such well-known producers as Cree, Inc. and LumiLEDs in the U.S.A. and Semi-LED in Taiwan. In order to be effective for the contamination reduction of in-line catheters and tubing, the emission of the high-power LED should be optimized in such way that the emission band of the LED will overlap the absorption bands of porphyrins and/or FAD. Another possible light source is a laser diode. Laser diodes at wavelengths such as 400-410 nm and 440-450 nm are available from Nichia in Japan.

According to the present invention, a high-power LED or a laser diode that emits in the violet/blue spectral region is installed in or attached to an in-line catheter, tubing, a stopcock valve, a manifold, a stopcock valve assembly, a connector, or other device associated with an intravenous therapy system, either in a permanent way, e.g., by embedding the LED or laser chip (possibly with their assemblies) inside a plastic body of the device (provided that accessible means for electrically connecting the device are provided), or in an impermanent way, e.g., by attaching the LED or laser chip (possibly with their assemblies) using an external clip or other attachment means or by inserting the chip into a slot or recess formed in a plastic body. The in-line catheters, tubing, connectors and stopcock valves are typically produced from flexible and rigid transparent polymers such as polycarbonate, polysulfone, polystyrene, polyvinyl chloride, Tygon® plastic, fluorinated carbon compounds, poly(methyl methacrylate) and others. These materials are transparent at the visible part of the spectrum; therefore violet and/or blue light can be transmitted through these materials from the LED or laser chip to the location of potential microorganism contamination. Although some attenuation of the violet and/or blue light in the elastomer material occurs, such attenuation is not so great (since the optical path is a few millimeters in most cases) as to interfere with delivery of the level of irradiation with violet and/or blue light required to effectively target the contamination reduction site. This cannot be achieved with UV light, which is highly absorbed in the plastics.

Moreover, since the elastomeric tubing material has an index of refraction of about 1.5, which is much higher than the index or refraction of air and of the aqueous physiological solutions filling the transfusion system, the light injected into the tubing material will travel through its walls according to the principle of total internal reflection similarly to what occurs in optical fibers. This transmission window of plastic materials does not exist in the ultraviolet (UV) range, so a similar contamination reduction effect cannot be achieved using UV LEDs: UV light propagating into the tubing system will be immediately attenuated and therefore be practically ineffective. On the other side of the spectrum, the green, red or NIR LEDs will be much less effective since, as shown in FIGS. 1 and 2, the absorption of FAD and porphyrins at these wavelengths is much lower and therefore these wavelengths are less effective for in-line tubing contamination reduction.

An additional advantage of contamination reduction of in-line tubing or other IV elements using violet or blue light is human safety. The violet and/or blue light is safe to medical personnel and patients, whereas a similar device based on UV irradiation would be unsafe for the users.

FIG. 3 is a graph showing the normalized power versus wavelength of light emitted by various commercially available LED products. As can be seen in FIG. 3, these LED products emit the desired wavelengths of light in the violet/blue spectral region. In addition, these LED products are relatively inexpensive so they can be used not only for externally attachable contamination reduction fixture device but even as an integral part of the in-line plastic tubing, manifold port, cap, or stopcock valve assembly. Therefore the contamination reduction LED or laser diode disclosed herein can be a disposable product, as are the connectors and hubs of the IV therapy system.

Because LEDs or laser devices operate on a low voltage, the power supply line to the LEDs or laser devices attached to the in-line tubing is safe to users, unlike other light contamination reduction means such as a mercury lamp that normally requires a high-voltage power supply. Moreover, UV lamps produce a great amount of heat as an inevitable side effect. LEDs or laser diodes, on the other hand, are highly efficient light sources and their heat production is low.

The contamination reduction process taught herein requires a relatively short irradiation time, after which the microorganisms have been eradicated and the irradiation may be stopped for some longer period until the microorganisms may grow again. Therefore the LED or laser diode irradiation can be applied in a low duty cycle way. This optional low duty cycle irradiation contamination reduction mode enables significant reduction in the power supply requirements. The electrical wire power supply line can be replaced by an alternative power supply structure based on energy delivered through optical fibers, or by inexpensive plastic optical fibers (POFs) and a photovoltaic cell that receives light energy and converts it into electrical energy that is accumulated in a small rechargeable battery or capacitor during the OFF period of the contamination reduction cycle. Another option is to use a wireless transformer power supply, such as is used in electric toothbrush chargers. These alternative power delivery methods provide enhanced safety to the user and reduced system deployment costs. A special benefit is the reduction of the so-called spaghetti effect of medical tubing since the fiber optic power delivery system may be embedded into the plastic tubing itself.

The present invention has particular application to individual stopcock valves as well as stopcock valve assemblies. A typical structure of a medical stopcock valve assembly is disclosed in U.S. Pat. No. 4,566,480 ("'480 patent"), the disclosure of which is incorporated by reference herein in its entirety. The '480 patent discloses a medical stopcock valve assembly comprising a valve body with extending fluid-directing tubes, at least some of which have a female Luer lock fitting adapted to receive a Luer lock cap. The '480 patent further discloses that various types of conventional caps or other closure devices other than a Luer lock cap may be employed, such as a plain, non-threaded cap having no male projecting portion, and, similarly, various types of conventional female fittings other than the flanged-type Luer lock fitting which are also adapted to receive a Luer lock cap or other cap or closure device may be employed in a typical stopcock valve assembly, such as a threaded screw-type, non-flanged fitting or a non-flanged, non-threaded cylindrical tubular extension, both of which are equally capable of receiving and retaining a Luer lock cap.

As used herein, the term "manifold" comprises a manifold fluid tube through which fluid flows. A manifold typically has a proximal end and a distal end. At the distal end of the manifold is a rotating adaptor which connects a catheter to the manifold and through which fluids pass intracorporeally to a patient. A manifold can be provided with a plurality of stopcock valves spaced along its length. The stopcocks each have a handle thereon which is rotated to direct the flow of fluid through the manifold. In order to operate a stopcock to stop a fluid from passing through the stopcock, the associated handle is turned toward a fluid line so as to point at the fluid line. When so pointed, the stopcock valve closes and prevents fluid in the pointed at line from passing through the stopcock. However, as used herein, the term "manifold" is not limited to structures comprising stopcock valves, but rather includes any structure comprising at least one tube and two or more valves for facilitating fluid communication between one or more sources of fluid and a catheter when the valves are open.

Figure 4:
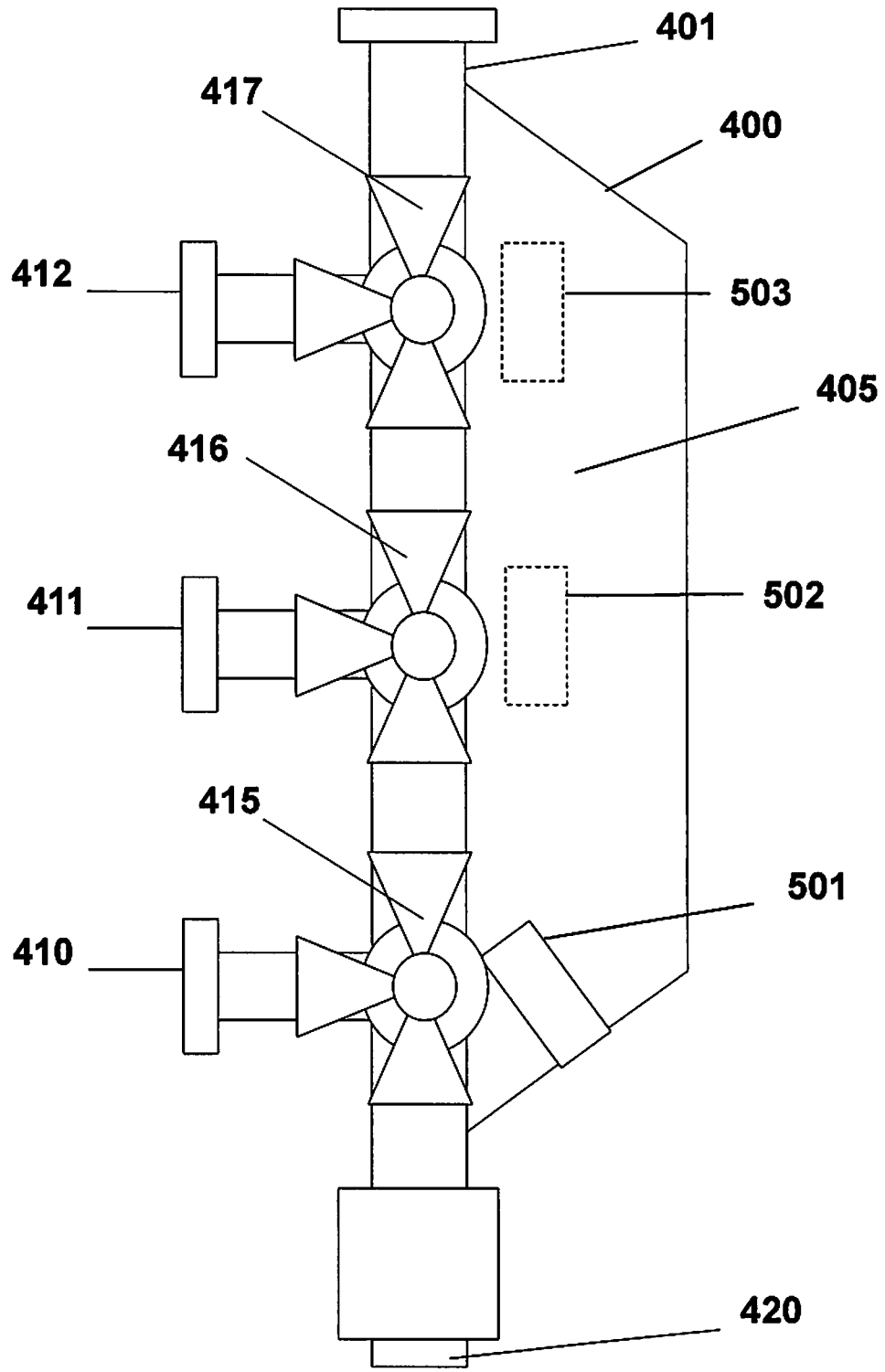
FIG. 4 is a drawing showing an elevation view of a typical plastic line tubing stopcock valve assembly in accordance with a first embodiment of the invention, wherein one or more diodes are installed in or attached to a manifold flange, the diodes being oriented to emit violet and/or blue light toward respective stopcock valves.

FIG. 4 shows the typical plastic line tubing stopcock valve assembly 400. In this example, the assembly comprises a manifold tubing 401, a manifold flange 405, several inlets 410, 411, 412, and several stopcock valves 415, 416, 417. The outlet connector 420 enables connection of tubing to the assembly.

According to a first embodiment of the invention, a first LED or laser diode 501 (depicted by solid lines in FIG. 4) is embedded or installed in the manifold flange 405. Diode 501 is oriented so that it emits violet and/or blue light over an area that includes the stopcock valve 415 and the portion of the manifold tubing below stopcock 415. The stopcock assembly 400 may comprise one or more slots for LED or laser diode integration. For example, the diode 501 can be inserted in a recess formed in the manifold flange 405. The diode 501 requires an electrical power supply (not shown in FIG. 4). Optionally, the diode 501 may be powered by batteries. Other schemes for providing electrical power to the diode 501 will be described below with reference to FIGS. 7-14.

Figure 5:
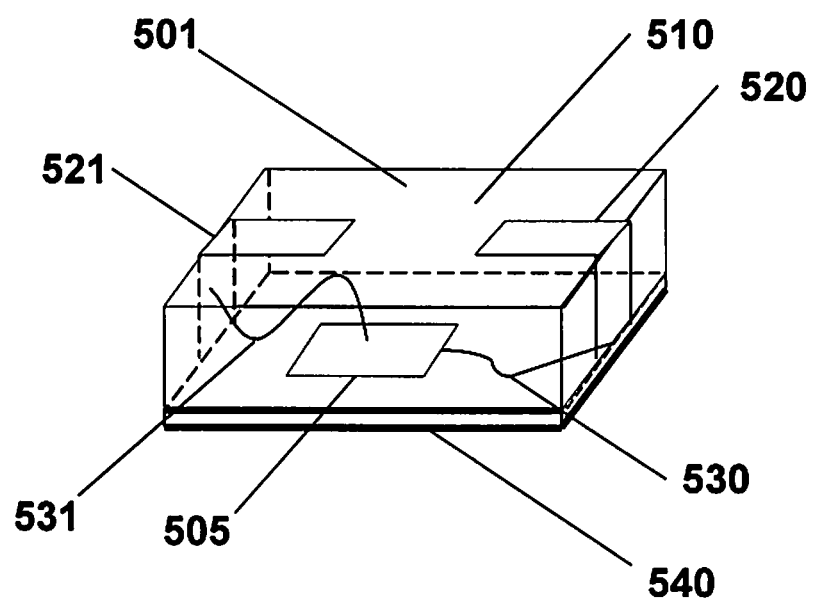
FIG. 5 is a drawing showing an isometric view of a violet and/or blue light-emitting diode suitable for use with the stopcock valve assemblies disclosed herein.

The LED or laser diode device 501 is shown in more detail in FIG. 5. The LED or laser diode device 501 may be similar in design to the standard SMD LED or laser diode devices. An LED or laser diode chip 505 is embedded in a plastic housing 510. The plastic housing includes macroscopic electrically conductive contacts 520, 521 electrically connected to the LED or laser diode chip by means of bonding wires 530, 531. The LED or laser diode emitter is facing the opposite to the electrical contacts side of the housing. The plastic housing 510 may include a snap feature 540 that enables simple snapping of the LED or laser diode device into its place inside the stopcock valve assembly 400 at the appropriate slot for a LED or laser diode chip.

Figure 6:
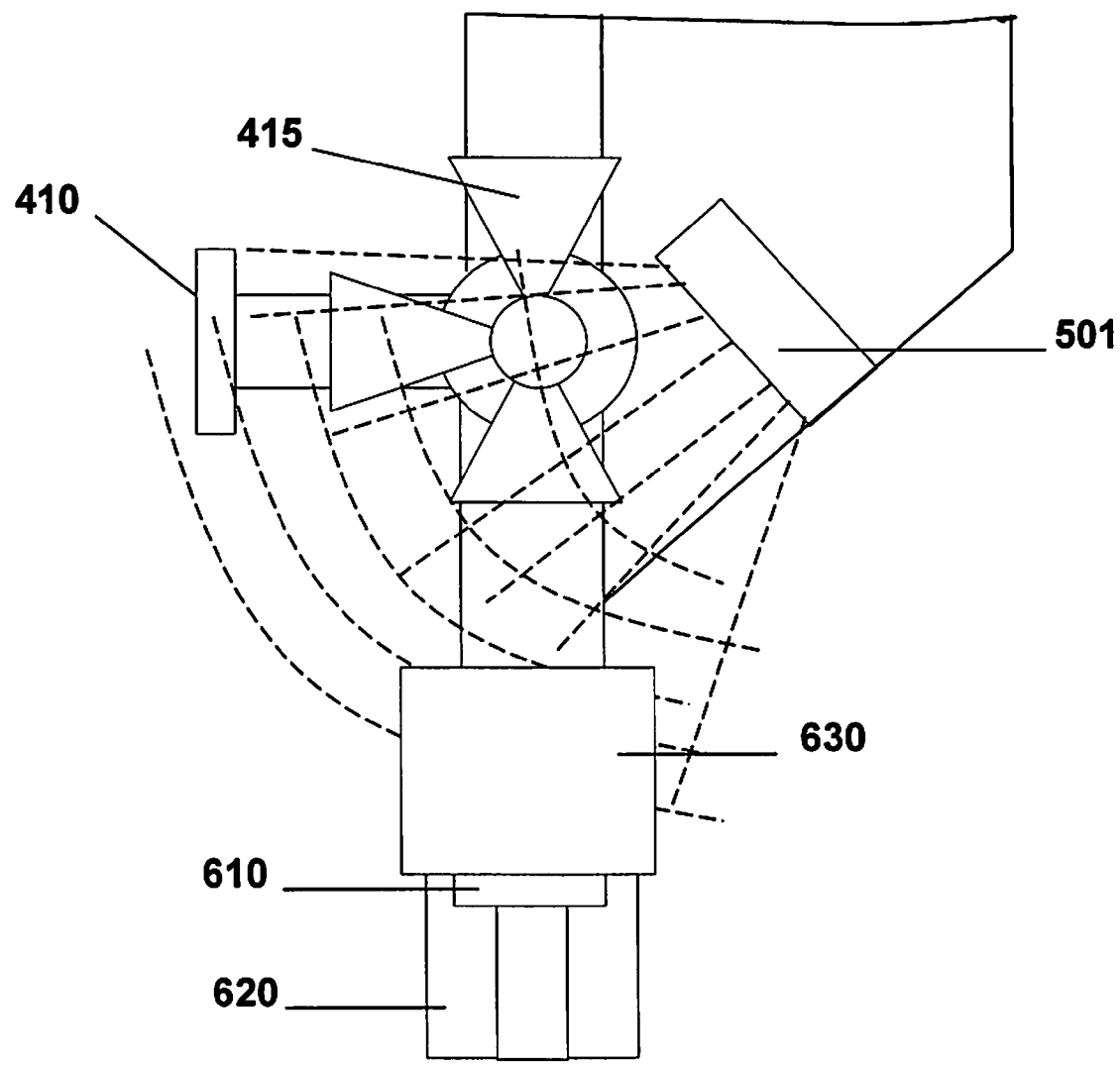
FIG. 6 is a drawing showing in greater detail a lowermost portion of the assembly depicted in FIG. 4.

FIG. 6 shows in more detail the irradiation path of the violet and/or blue light emitted by the LED or laser diode 501. The Luer male part 610 is connected into the Luer female part 620 and fixated by means of the nut 630. The LED or laser diode device 501 (snapped into a special slot) irradiates the stopcock valve 415 and the whole connection assembly (610, 620, 630) with violet and/or blue light.

Preferably the LED or laser diode chip 505 emits light in a wavelength band centered between 400 and 492 nm. Alternatively the LED or laser diode device 501 can comprise several LED or laser diode chips emitting light at the same wavelength or several LED or laser diode chips emitting light at respective wavelengths to better cover the absorption of FAD and the porphyrins. The LED or laser diode device can be an LED or laser diode array. Alternatively several LED or laser diode devices 501 (indicated by solid lines in FIG. 4), 502 and 503 (indicated by dashed lines in FIG. 4) may be used in the same stopcock valve assembly 400 to achieve better positioning of the LEDs or laser diodes relative to respective target irradiation sites or stopcock valves. In the example shown in FIG. 4, diode 502 irradiates stopcock valve 416 and inlet 411, while diode 503 irradiates stopcock valve 417 and inlet 412.

Figure 7:
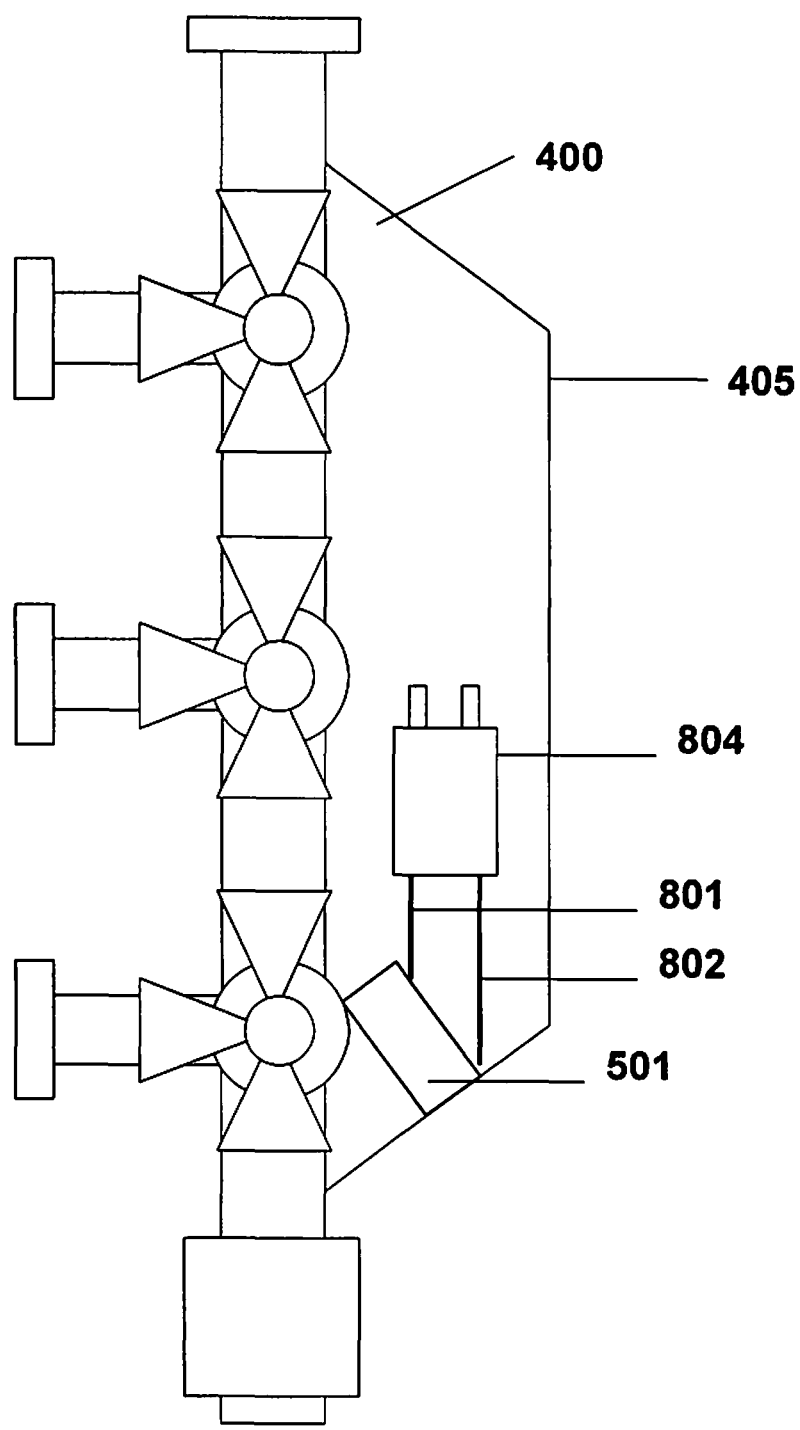
FIG. 7 is a drawing showing an elevation view of a stopcock valve assembly in accordance with a second embodiment, with an electrical power connector embedded or installed in or attached to the manifold flange for supplying power to a light-emitting diode.

FIG. 7 shows a stopcock valve assembly in accordance with a second embodiment. In addition to a diode 501, the assembly comprises an electrical power connector 804 embedded or installed in or attached to the plastic manifold flange 405 of the stopcock valve assembly. The snapped-in-place LED or laser diode device 501 is electrically connected through a pair of electrically conductive contacts (i.e., contacts 520, 521 seen in FIG. 5) to a pair of conducting wires 801, 802, which in turn electrically connect the diode 501 to the electrical power connector 804. The conducting wires 801, 802 are also either embedded or installed in or attached to the manifold flange 405. The electrical power connector 804 comprises a pair of terminals which fit inside a socket (not shown in FIG. 7) that is electrically connected to an electrical power supply (not shown).

Figure 8:
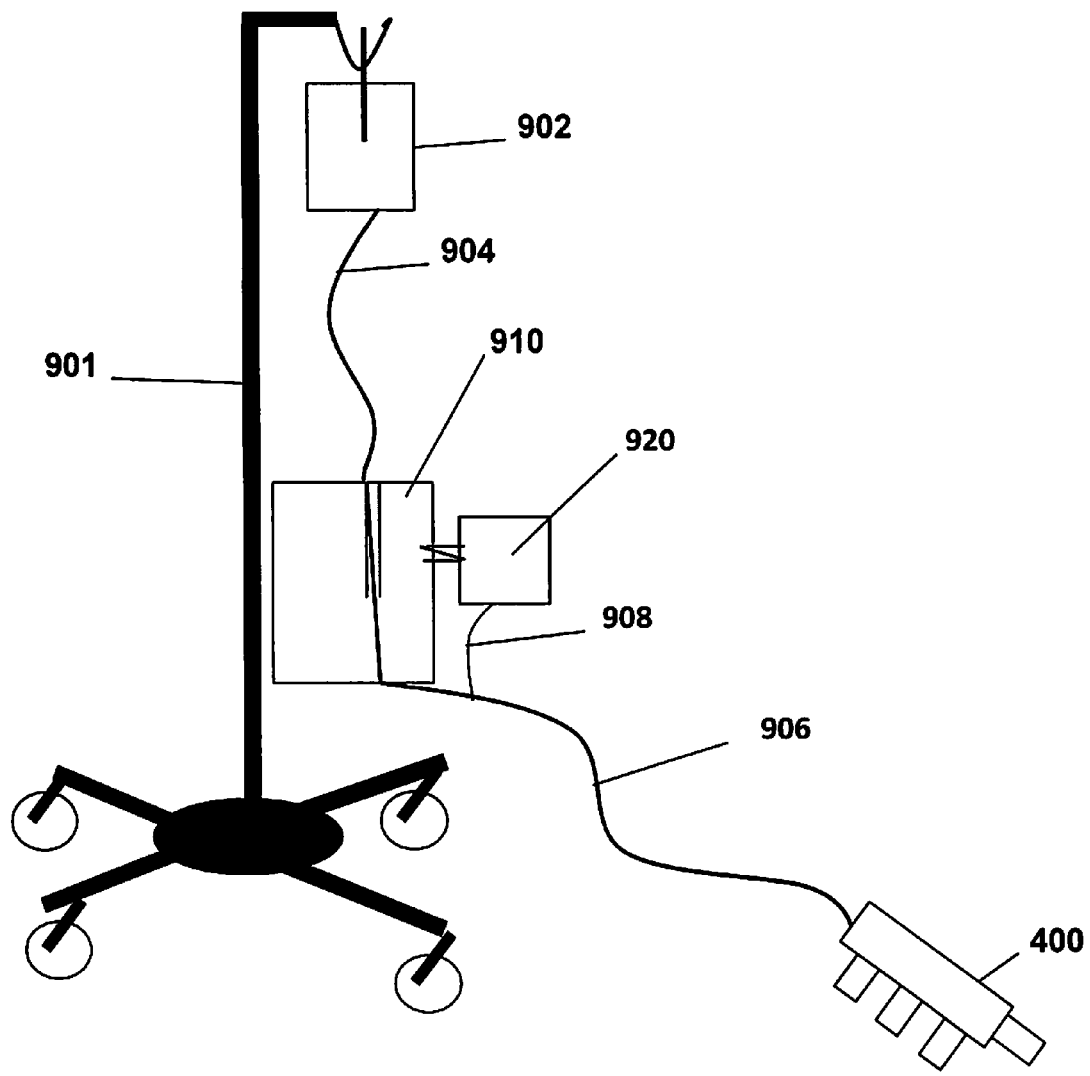
FIG. 8 is a drawing showing an intravenous therapy setup that incorporates a stopcock valve assembly in accordance with the second embodiment.

FIG. 8 shows an intravenous therapy setup that incorporates a stopcock valve assembly in accordance with the second embodiment. The setup comprises a wheeled IV pole 901, a bag of fluid 902 hanging from a hook of pole 901, a tube 904 for feeding the fluid from bag 902 to a medical patient, and a standard drop counter 910. FIG. 8 also shows a LED or laser diode power delivery system for delivering power to the diode or diodes incorporated in or attached to the stopcock valve assembly 400. The diode power delivery system comprises an LED or laser diode driver 920 which is attached to the drop counter 910. The LED or laser diode driver 920 comprises a self-contained power supply that has a driver circuit that matches the electrical output to the electrical characteristics of the diode. Alternatively, the diode driver 920 can get its electrical power from the drop counter, which is electrically powered. Alternatively, the diode driver 920 can be electrically connected to an electrical outlet or other source of electrical power.

Figure 9:
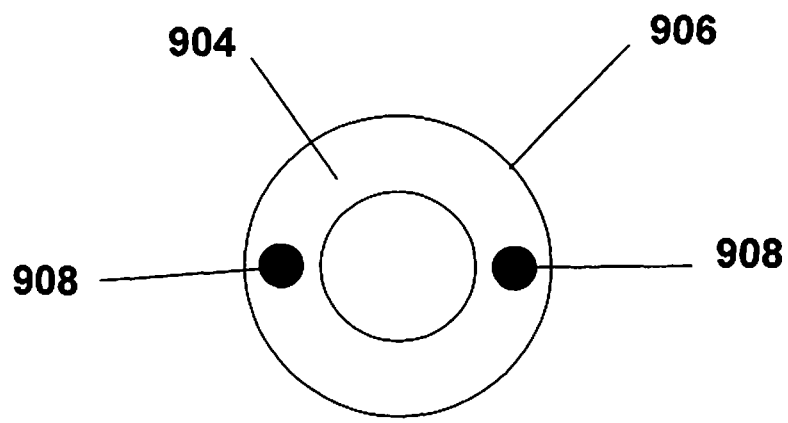
FIG. 9 is a drawing showing a sectional view of a tube with embedded electrically conductive wires.
Figure 10:
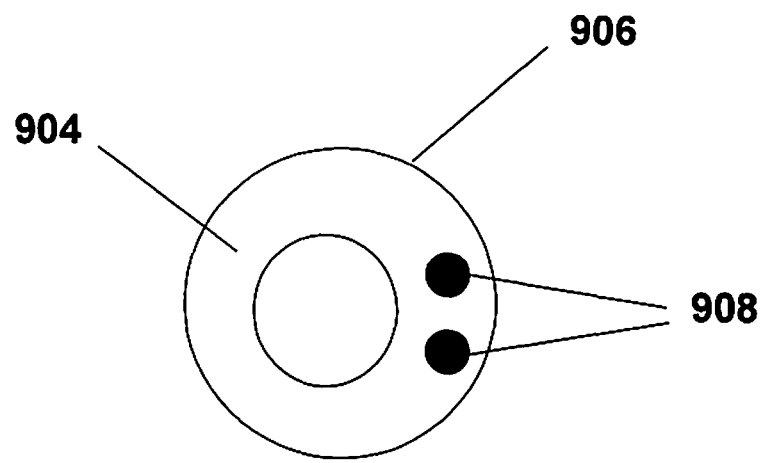
FIG. 10 is a drawing showing a sectional view of a tube with embedded electrically conductive wires.
Figure 11:
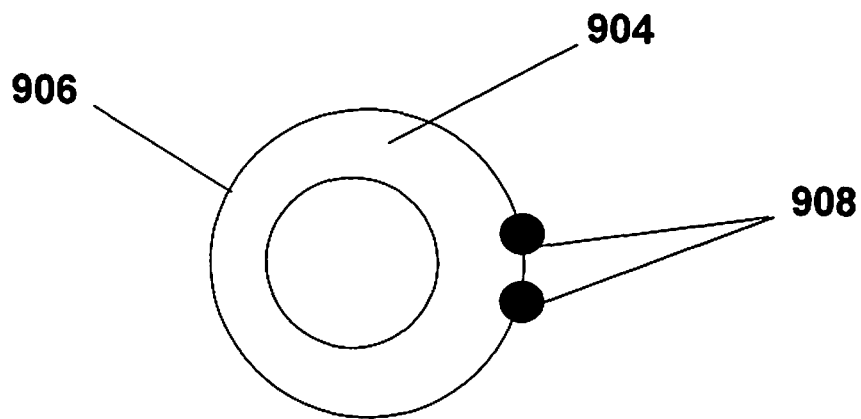
FIG. 11 is a drawing showing a sectional view of a tube with electrically conductive wires attached to the outside of the tube.

Still referring to FIG. 8, the electrically conductive power supply line 908 can be incorporated in the tubing 904. For example, the power supply line 908 may comprise electrical wires embedded in the wall of the tubing 904, as shown in FIGS. 9 and 10, the resulting structure being indicated by reference numeral 906. Alternatively, the electrical wires of a power supply line 908 may be attached to the exterior of the tubing 904, as shown in FIG. 11. Alternatively, the power supply wiring may be totally independent of the tubing (not shown in the drawings).

Figure 14:
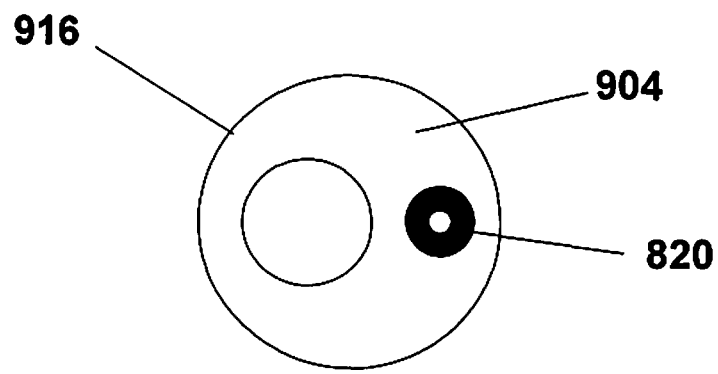
FIG. 14 is a drawing showing a sectional view of a tube with embedded optical fiber in accordance with the third embodiment.
Figure 12:
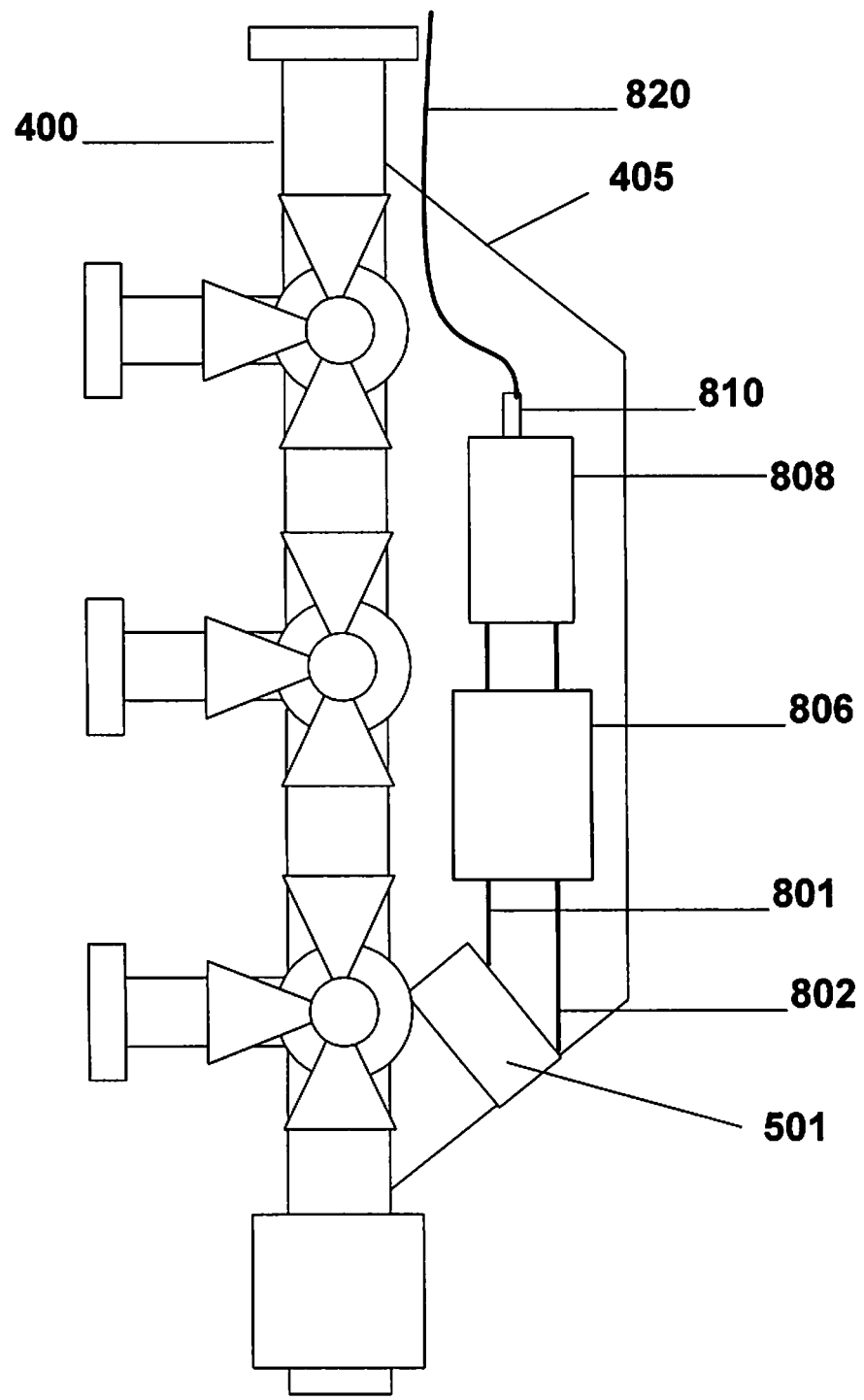
FIG. 12 is a drawing showing an elevation view of a stopcock valve assembly in accordance with a third embodiment, with an optical connector and a photovoltaic cell embedded or installed in or attached to the manifold flange for supplying power to a light-emitting diode.

In accordance with a third embodiment of the invention, the LED or laser diode power supply system may be accomplished by utilizing a fiber optic power delivery system, which will now be described with reference to FIGS. 12-14. FIG. 12 shows a manifold flange 405 of a stopcock valve assembly of the type previously described, with an electronic power system 806 and a photovoltaic cell 808 embedded or installed in or attached to the flange. The photovoltaic cell 808 receives light energy from a light source (not shown in FIG. 12) via an optical fiber 820 and an optical connector 810 which couples the output of the optical fiber 820 to an input of the photovoltaic cell 808. The terminal portion of the optical fiber 820 and the optical connector 810 are either embedded or installed in or attached to the manifold flange 405. The photovoltaic cell 808 converts the received light energy into electrical energy. The generated electric current flows from the photovoltaic cell 808 to the electronic power system 806, where the electrical current charges an energy storage device. The energy storage device may be a rechargeable battery or a capacitor. When the storage device is sufficiently full, an electronic diode driver circuit of the power system 806 electrically couples the energy storage device to the LED or laser diode 501, thereby enabling its operation (i.e., the emission of light in the violet/blue spectral region) for a predetermined time period.

Figure 13:
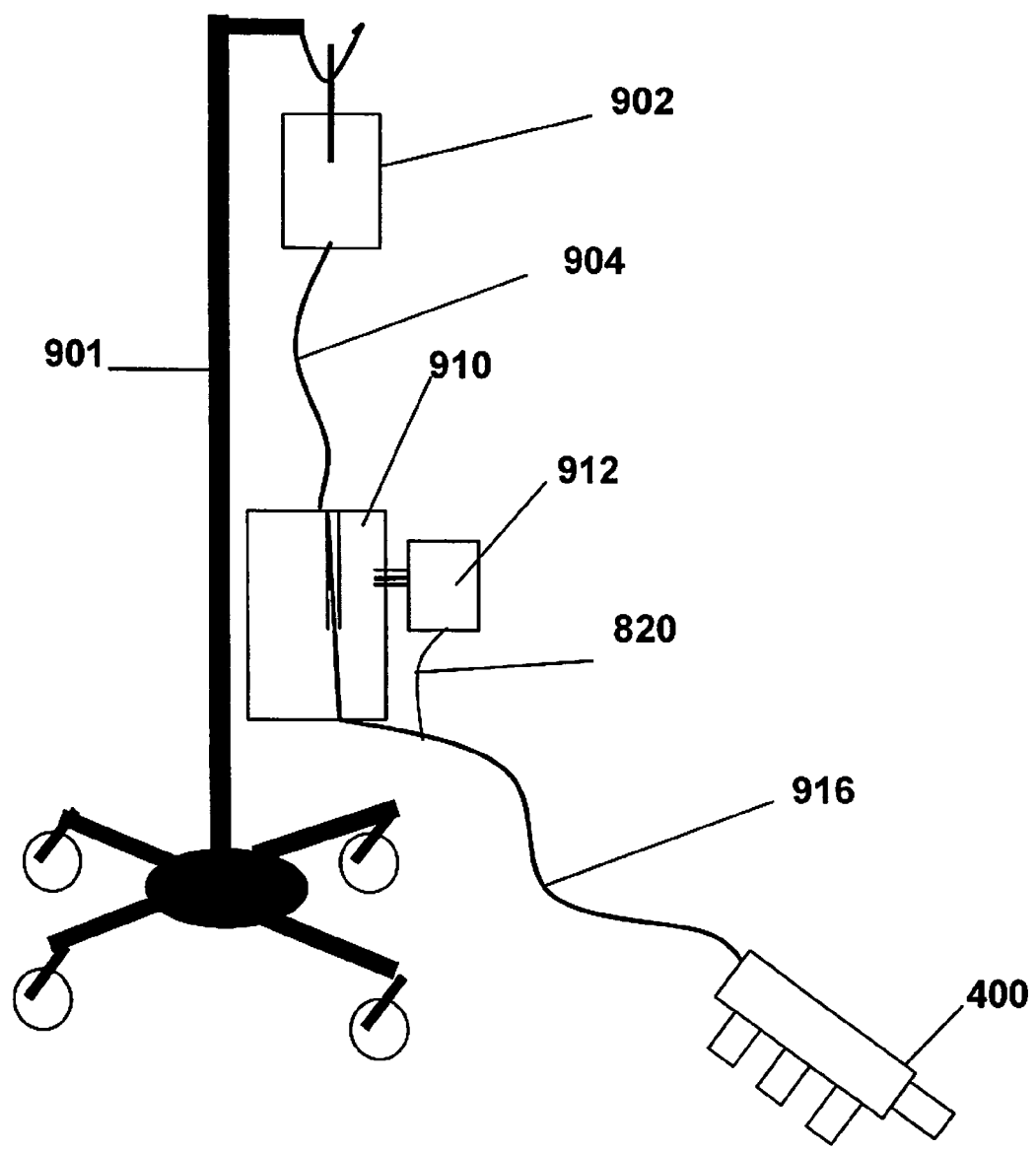
FIG. 13 is a drawing showing an intravenous therapy setup that incorporates a stopcock valve assembly in accordance with the third embodiment.

Other parts of the fiber optic power delivery system are shown in FIG. 13, which shows an intravenous therapy setup that incorporates a stopcock valve assembly in accordance with the third embodiment. As previously described, the setup comprises a wheeled IV pole 901, a bag of fluid 902, a tube 904 for feeding the fluid from bag 902 to a medical patient, and a standard drop counter 910. FIG. 13 also shows a fiber optic power delivery system for delivering light energy to a photovoltaic cell incorporated in or attached to the stopcock valve assembly 400, as described with reference to FIG. 12. The fiber optic power delivery system comprises a light source 912, such as a laser or high-power LED, which is attached to the drop counter 910. The wavelength of the light source 912 (shown in FIG. 13) is optimized to be at the highest efficiency of the photovoltaic cell 808 (shown in FIG. 12). The light source 912 can optionally get its electrical power from the drop counter. Alternatively, the light source 912 can be electrically connected to an electrical outlet or other source of electrical power. The output of the light source 912 is optically coupled to the photovoltaic cell of the stopcock valve assembly 400 by means of the aforementioned optical fiber 820. The optical fiber 820 can be embedded in the tubing 904, as shown in FIG. 14, the resulting structure being indicated by reference numeral 916. Alternatively, the optical fiber can be attached to the exterior of the tubing.

In accordance with a fourth embodiment, the light source is attached to the line by means of a clip or other temporary fixation means. For example, a removable clip device having an LED or laser diode chip installed therein or attached thereto can be temporarily affixed to a connector or tube of a manifold. Such temporary fixation enables reuse of the device multiple times and may be cost effective.

Figure 15:
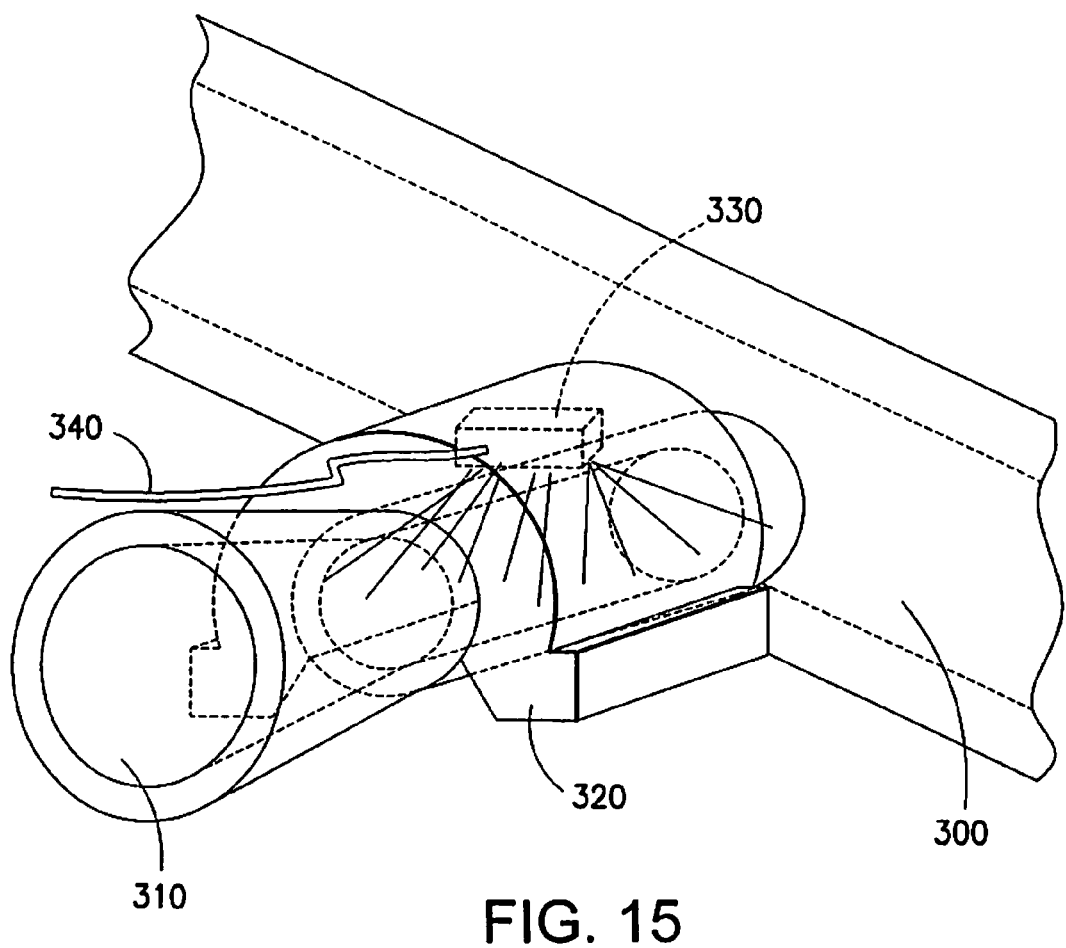
FIG. 15 is a drawing showing an isometric view of a diode mounted on a Luer connection to an IV system element by means of a clip in accordance with a fourth embodiment.

One example of a removable device in accordance with the fourth embodiment is shown in FIG. 15. An LED assembly 330 is embedded or installed in or attached to a flexible plastic dip 320. In this example, the clip 320 has a U-shaped profile that allows it to be fitted snugly onto the neck of a Luer connection 310 of any IV system plastic element 300 (e.g., a manifold or stopcock valve assembly). The snap-on clip 320 is easy to install and remove by hand, yet it is securely attached to the neck of the Luer connection 310. In particular, the clip may consist of a molded piece of plastic comprising a section of a circular cylinder having a longitudinal slot flanked by a pair of oppositely directed flanges, as seen in FIG. 15. The LED assembly 330 can be electrically connected to an external power source (not shown) by a low-voltage DC power cable 340 which provides the electrical energy to the LED needed to emit the bactericidal radiation (e.g., light in the violet/blue spectral region). Alternatively, the LED assembly may include batteries to power the device. The LED assembly emission angle is designed to cover areas of stagnation, including stagnation areas in the vicinity of the junction of Luer connection 310 and IV element 300.

The cable 340 may connect to a controller (not shown), which controller may have multiple sockets on its front panel for receiving respective plugs of multiple cables that power multiple light-emitting devices directed at multiple stagnation zones of the IV set. The controller will also include the power supply and LED driver. It will have an ON/OFF switch and simple indicators and 7-segment displays to indicate the illumination parameters. The controller may further comprise manually operable switches for turning respective light-emitting devices ON or OFF, as well as electronic circuitry for turning the illumination ON and OFF in accordance with predetermined duty cycles. In particular, the controller may comprise a processor programmed to control a multiplicity of light-emitting devices in accordance with an illumination regime of duty cycles.

In accordance with a fifth embodiment, a plurality of light sources may be installed on a manifold flange of a stopcock valve assembly 400 by means of a mounting plate 830. The mounting plate 830 may have one or more LED or laser diode chips 840 installed therein or attached thereto. The chips 840 may be powered in conventional manner via electrical conductors (not shown) which electrically connect the chips to an electrical connector 850, which is also embedded or installed in or attached to the mounting plate 830. The mounting plate 830 may take the form of a printed circuit board with chips 840 mounted on a surface thereof. The electrical connector 850 is electrically connected to a power supply (e.g., a controller of the type previously described with reference to FIG. 15) by means of electrical wiring 860. Alternatively, the power supply to the LEDs or laser diodes on the mounting plate may be accomplished by any of the means previously described, including the fiber optic energy delivery system shown in FIG. 13.

Figure 16:
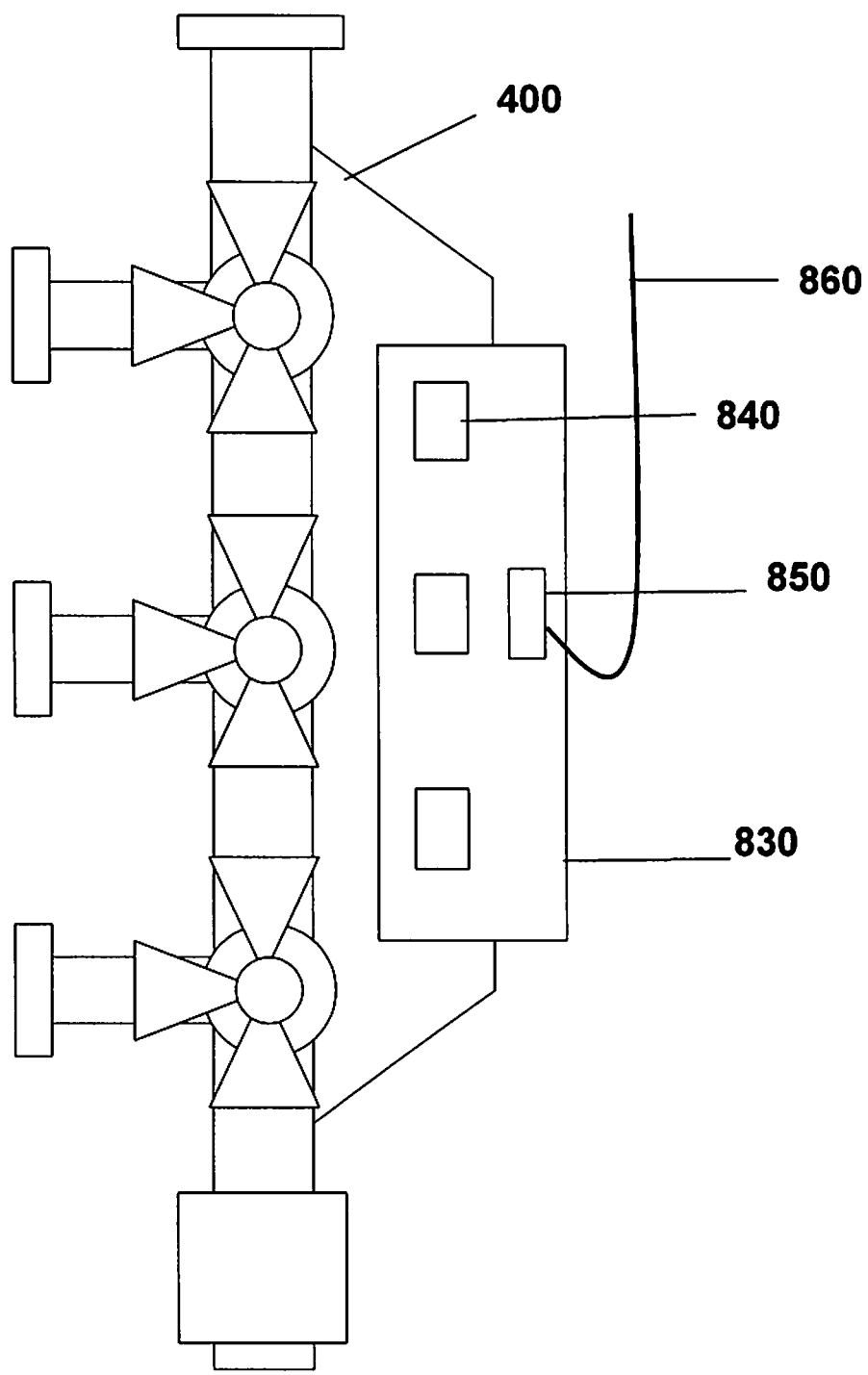
FIG. 16 is a drawing showing an elevation view of a stopcock valve assembly that has a plate carrying an array of diodes mounted to a manifold flange of the assembly in accordance with a fifth embodiment.

The device shown in FIG. 16 is cost effective since it can be reused multiple times on different equipment. The mounting plate 830 may be attached to the manifold flange by means of clips, temporal adhesive or any other means providing a convenient fixation of the device while allowing for removal after completion of a line usage cycle.

In accordance with a sixth embodiment, violet and/or blue light can be directed onto any zone of stagnation of a fluid transfer system, such as an intravenous therapy system, provided that the stagnation zone is accessible by an optical fiber. The optical fiber can be made from silica or from a polymeric material. Especially plastic optical fiber (POF) can be used as a cost-effective solution for light delivery. The distal end of the optical fiber may be shaped or provided with an optical element for dispersing light over the target area. The proximal end of the optical fiber is optically coupled to a source of violet and/or blue light, which may comprise a standalone unit. For example, an LED or a laser diode can be installed in a standalone housing, the light from this source being delivered to the target area by means of the optical fiber. Alternatively, the housing with the light source inside may be attached to the drop counter in a manner similar to what is depicted in FIG. 13. In accordance with a further example, the diodes 501, 502, 503 shown in FIG. 4 could be replaced by distal ends of respective optical fibers, each receiving violet and/or blue light from a remote source not installed in or attached to the stopcock valve assembly. The distal ends of the optical fibers can be oriented such that light emanating therefrom is respectively directed onto the stopcock valves 415, 416, 417 and stagnation zones associated therewith. As previously described, each optical fiber can be a standalone fiber or it can be part of the tubing in such a way that the optical connection is accomplished along with the connection of the tubing.

Figure 17:
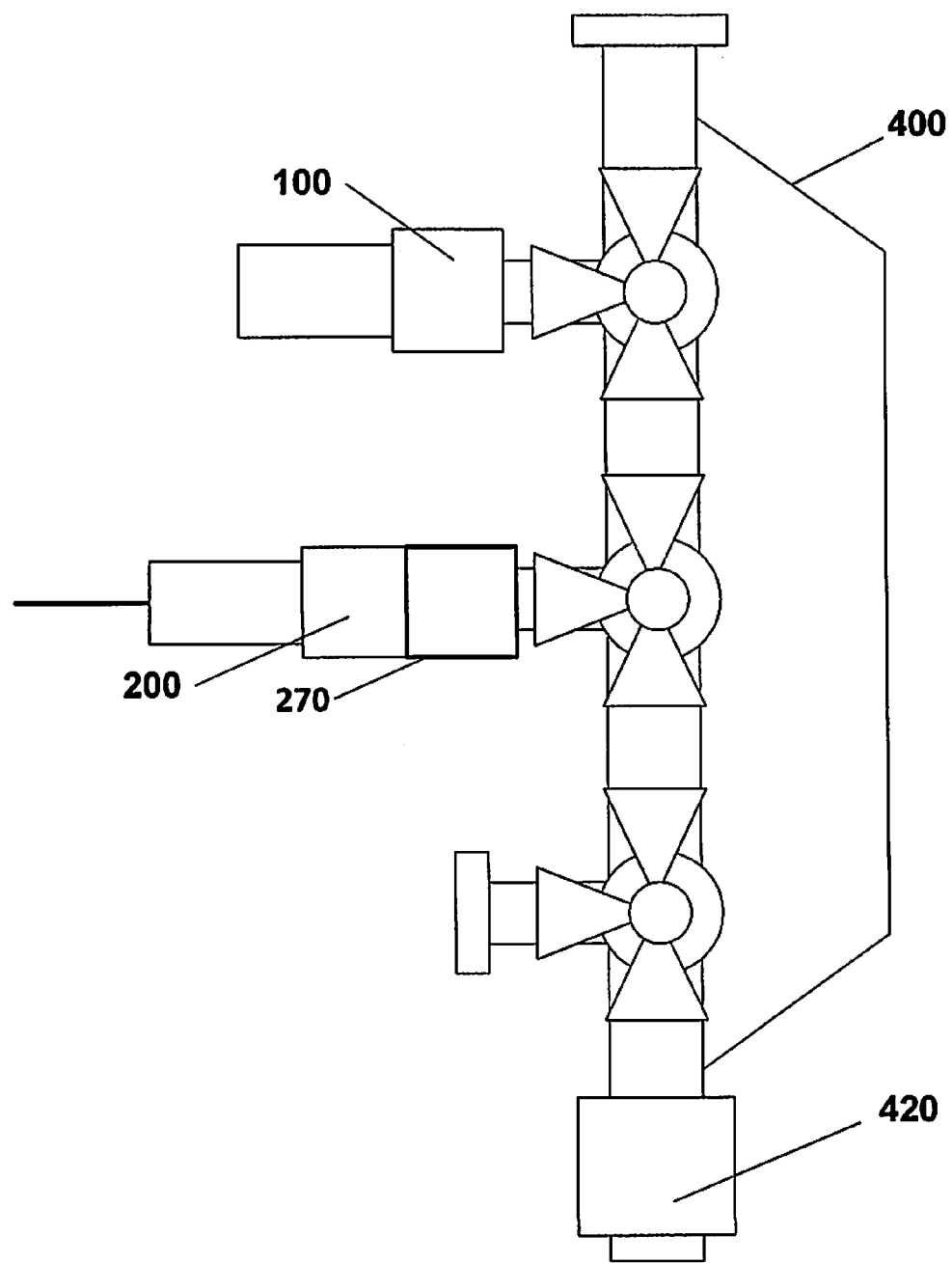
FIG. 17 is a drawing showing an elevation view of a stopcock valve assembly having respective ports capped by light-emitting devices in accordance with seventh and eighth embodiments respectively.

FIG. 17 shows a port or stopcock valve assembly (previously described with reference to FIG. 4) having ports of respective inlets capped by light-emitting devices 100 and 200 in accordance with alternative (i.e., seventh and eighth) embodiments. The device 100 can be coupled to the open port of an inlet of the IV set so that the inlet port is covered and light emitted by device 100 is directed toward the stopcock valve associated with that inlet. The device 200 can be coupled onto one end of a flow-blocking yet transparent adapter 270, the other end of the adapter being coupled to the open port of an inlet of the IV set. In this case adapter 270 covers and closes the inlet port and light emitted by device 200 is directed toward the stopcock valve associated with that inlet. The semi-disposable cap 200 should not, and does not fit the Luer port of the IV set. There must be a mediating adapter 270. This is done since the semi-disposable cap 200 is not sterile (at least after its first use); therefore it should not come into direct contact with the IV port. The adapter 270 will have a Luer fitting on one end for coupling with the IV set and another fitting (other than Luer, e.g., threaded or bayonet) that fits inside the cap 200 on its opposite end.

FIGS. 18 and 19 are sectional views of a disposable light-emitting cap 160 in accordance with the seventh embodiment. In this case the bactericidal device is an extended Luer cap 100 comprising a plastic housing 102 that houses a LED or laser diode chip 110 powered by a plurality of batteries 140-142. The diode chip 110 is mounted on a surface of a PCB 130. When the cap 100 is coupled to an open end of a Luer connector, as shown in FIG. 19, light emitted by the diode chip 110 is transmitted by an integrated CPC (compound parabolic concentrator) optical lens 120 into the port of the Luer connector 312 and toward a valve or other stagnation zone of an IV set. The low cost of manufacture for this relatively simple device makes it "disposable" when the batteries 140-142 have been exhausted.

The cap 100 shown in FIGS. 17-19 serves both as a hermetic seal to an IV port and as a light-emitting device immediately after it is attached to a Luer port. The open end of plastic housing 102 has a Luer lock fitting and can be coupled directly to an open port of an IV set. The CPC lens 120 is specially designed to optimize the angle of the diverging light being emitted into the port, and can also be used as the activating element that is pressed while the cap is connected to the Luer element (as shown in FIG. 19), thus turning the LED on. Preferably, the PCB 130 includes an electronic circuit that will cut-off the supply of electrical power from the batteries to the diode chip after a predetermined time period, or to create chopping-mode illumination.

Optionally, a manually operated button could be provided on the exterior of the housing 102 for turning the illumination ON and OFF, the position of such button controlling the state of an ON-OFF switch circuit assembled on the PCB 130.

In accordance with the embodiment depicted in FIGS. 18 and 19, the light-emitting cap 100 is designed to turn ON when the cap 100 is pressed or screwed onto one end of a connector. More specifically, the diode chip 110 will be activated when the sterile disposable cap 100 is installed on an end of a Luer connector 312 (only partially shown in FIGS. 18 and 19). FIG. 18 shows the device in an OFF state, i.e., the cap has not been coupled to the end of the connector 312 yet, while FIG. 19 shows the device in an ON state, i.e., the cap has been fully coupled to the end of the connector 312. In accordance with the embodiment shown in FIGS. 18 and 19, the diode chip turns on automatically when the cap 100 is installed on an inlet end 314 of Luer connecter 312, eliminating human errors, such as forgetting to turn the light-emitting cap on.

The above-described diode activation is accomplished by constructing the lens 120 and PCB 130 as an integral unit (with the diode chip sandwiched therebetween) that is slidably installed inside a cylindrical chamber inside the housing 102. This integral unit will be axially displaceable inside the housing 102 between first and second axial positions, as respectively shown in FIGS. 18 and 19. Before the cap 100 is coupled to the end 314 of connecter 312, the lens/diode/PCB assembly is disposed at the first axial position shown in FIG. 18. In the first axial position, the electrical contact terminal on the rear face of the PCB 130 is separated from the contact terminal of battery 140, as a result of which the diode chip is receiving no electrical power and is turned OFF. When the cap 100 is fully coupled to the open end of connector 312, the end face 314 of the connector pushes the lens/diode/PCB assembly from the first axial position to the second axial position shown in FIG. 19. In the second axial position, the electrical contact terminal on the rear face of the PCB 130 is in contact the contact terminal of battery 140, as a result of which the diode chip is receiving electrical power and is turned ON. So long as the cap 160 remains coupled to the connector 312, the electrical circuit is closed, and according to the electronic controls in the PCB, the diode chip will continue to emit light.

The housing 102 may be provided with an annular flange 104 that projects radially inward in the housing chamber and acts as a stop. The annular flange 104 interacts with opposing limit surfaces of an annular groove formed on the outer periphery of the lens 120. When the flange 104 abuts the limit surface on the right-hand side of the annular groove (as seen in FIG. 18), the lens/diode/PCB assembly will be in the first axial position; and when the flange 104 abuts the limit surface on the left-hand side of the annular groove (as seen in FIG. 19), the lens/diode/PCB assembly will be in the second axial position. Conventional means (such as a second annular flange or a plurality of radially inwardly directed projections) may be provided on the internal surface of the housing 102 for limiting the movement of the batteries toward the open end of the cap 100. The spring 150 will urge the batteries toward and into abutment with those stopping means.

This disposable light-emitting cap 100 can be packed as single units inside a sterile pouch. The user will remove a sterile cap from the pouch and then couple the cap to a female port of the IV set. Upon installing the cap on the port, the light source can be turned on and will remain on for as long as planned. This device will be used as a cap as well for keeping the port sealed until the next use.

Figure 20:
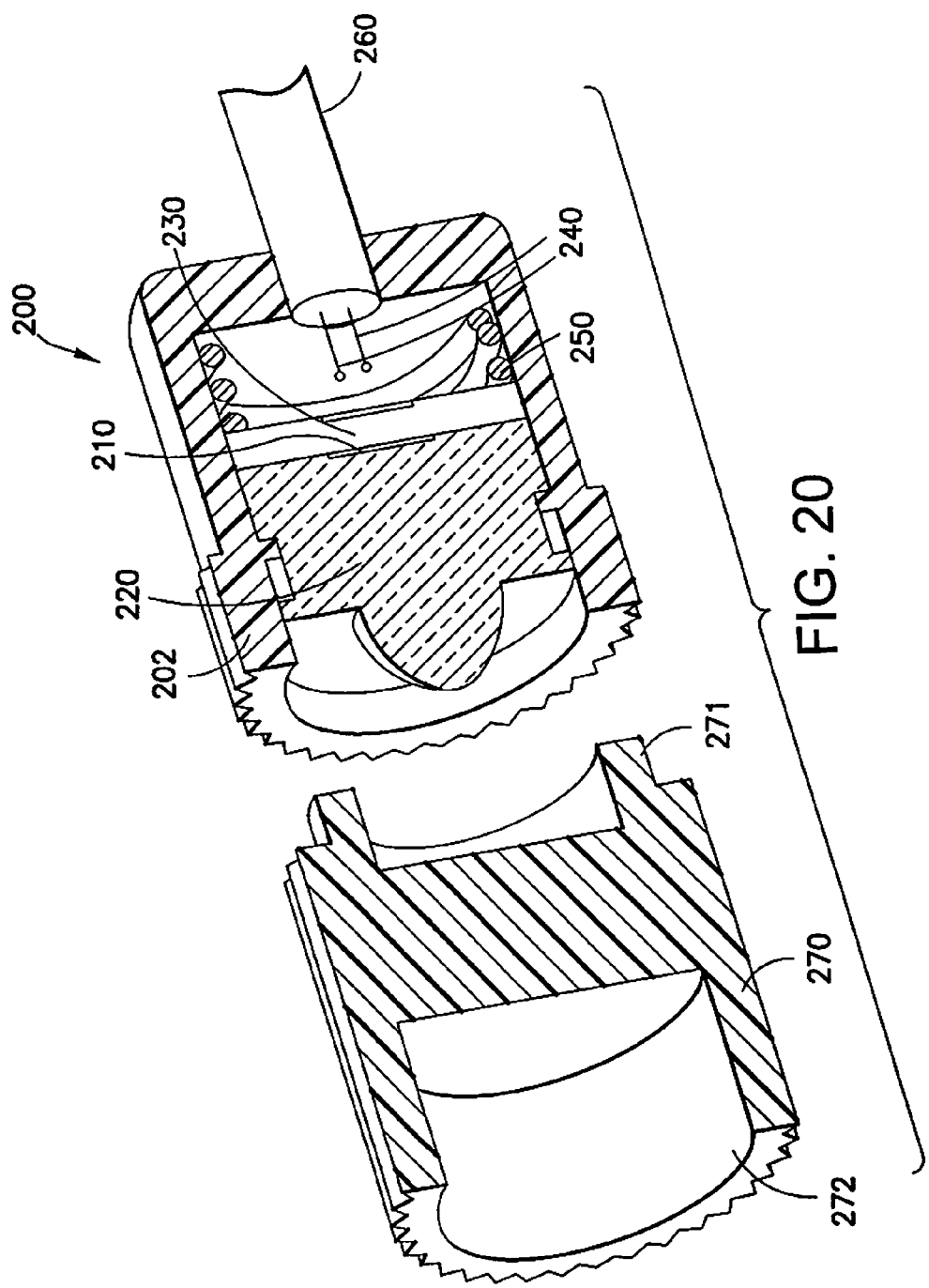
FIG. 20 is a drawing showing a sectional view of an adapter and a semi-disposable light-emitting cap in accordance with the eighth embodiment. In this case the light source is activated when the cap is installed on an end of the adapter.

FIG. 20 is a drawing showing a sectional view of a plastic adapter 270 and a semi-disposable light-emitting cap 200 having a plastic housing 202 in accordance with the eighth embodiment. In this example, the end 272 of adapter 270 has a Luer fitting for coupling with an open port of the IV set, while the other end 271 of adapter 270 has a non-Luer fitting for coupling with the non-Luer open end of the housing 202 of light-emitting cap 200. In this embodiment the housing 202 houses a LED or laser diode chip 210 mounted on a surface of a PCB 230. The cap 200 further comprises a CPC lens 220 which is shaped to optimally redirect the emitted light toward the open port of the IV set, and can also be used for activating the LED on, when it is pressed against end 271 of adapter 270. The cap 200 (i.e., the diode 210 and the PCB 230) is powered via an electrical cable 260, the internal wires of which connect to a pair of electrically conductive contact terminals 240. In the uninstalled state, the contact terminal of the PCB 230 is separated from the contact terminals 240 by a gap, so that the light-emitting diode is receiving no electrical power. When the cap 200 is installed on end 271 of the adapter 270, the end face of end 271 bears against the CPC lens 220, causing the lens/diode/PCB assembly to move toward the terminals 240 until the contact terminal on the back surface of the PCB 230 contacts terminals, thereby providing electrical power to the diode and PCB. The limited axial sliding of the lens/diode/PCB assembly may be accomplished by providing housing 202 with an annular flange 204 that projects inwardly into an annular groove formed on the outer periphery of the CPC lens 220. A similar structure has already been described with reference to FIGS. 18 and 19 and such description is not repeated here.

In accordance with a variation of the eighth embodiment, instead of constructing the light-emitting cap 200 so that it illuminates in response to being coupled to an open port at the end of a connector, the cap 200 may be electrically connected to a controller of the type previously described with respect to FIG. 15. Such controller may comprise manually operable switches for turning respective light-emitting caps ON or OFF, as well as electronic circuitry for turning the illumination ON and OFF in accordance with predetermined duty cycles. In particular, the controller may comprise a processor programmed to control a multiplicity of light-emitting devices in accordance with an illumination regime of duty cycles.

If necessary, a heat sink can be provided inside the housing 202 to dissipate heat generated by the diode chip. For example, the PCB 230 may be made of aluminum and may itself be a heat sink.

In accordance with the embodiment shown in FIG. 20, the adapter 270 is initially sterile and intended to be used only once, while the light-emitting cap 200 is intended to be used multiple times. Preferably, the adapter is made of injection-molded standard medical transparent plastic material (e.g., polycarbonate), individually packed and sterilized. After the adapter has been used on an IV set, it can be disposed of, whereas the light-emitting cap 200 can be reused.

The structures disclosed herein also have application in systems wherein the bactericidal radiation is light having a wavelength outside the violet/blue spectral region.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

The invention claimed is:

1. A system for reducing the count of infectious agents in an intravenous access system, comprising:
   an intravenous access system comprising first and second portions;
   an optical element that is capable of transmitting light in or on said first portion of said intravenous access system, said optical element being placed so that transmitted light will be directed toward said second portion of said intravenous access system;
   a source of light optically coupled to said optical element, wherein said light source emits light, said emitted light being transmitted by said optical element toward said second portion of said intravenous access system, wherein said emitted light has a bactericidal effect;
   a housing configured to attach to an inlet of said first portion of said intravenous access system;
   a printed circuit board movable within said housing between first and second positions; and
   a first contact terminal disposed inside said housing and connected to a source of electrical power,
   wherein said printed circuit board has a second contact terminal mounted on a rear surface thereof, said light source is mounted on a front surface of said printed circuit board, and an electronic circuit connected to said second contact terminal and to said light source;
   said an optical element is attached to said front surface of said printed circuit board and optically coupled to said light source;

said contact terminals are not in contact when said printed circuit board is at said first position and are in contact when said printed circuit board is at said second position; and said light source emits light comprising wavelengths in a range from 390 to 492 nm when said first and second contact terminals are in contact and said electronic circuit electrically connects said second contact terminal of said printed circuit board to said light source.

2. The system as recited in claim 1, wherein said light source is a semiconductor diode.

3. The system as recited in claim 1, wherein said optical element is a lens.

4. The system as recited in claim 1, wherein said source of electrical power comprises a rechargeable battery, further comprising a photovoltaic cell electrically coupled to said rechargeable battery.

5. The system as recited in claim 1, wherein said electronic circuit is capable of cutting off the supply of power to said light source at a predetermined time subsequent to activation.

6. The system as recited in claim 1, wherein said electronic circuit is capable of controlling said light source to produce chopping-mode illumination.

7. The system as recited in claim 1, wherein said optical element comprises an outer periphery having an annular groove.

8. The system as recited in claim 1, wherein said optical element comprises a compound parabolic concentrator lens.

9. A system for reducing the count of infectious agents in an intravenous access system, comprising:

an intravenous access system comprising first and second portions;

an optical element that is capable of transmitting light in or on said first portion of said intravenous access system, said optical element being placed so that transmitted light will be directed toward said second portion of said intravenous access system;

a source of light optically coupled to said optical element, wherein said light source emits light, said emitted light being transmitted by said optical element toward said second portion of said intravenous access system, wherein said emitted light has a bactericidal effect;

an adapter having a Luer fitting on one end for coupling to an inlet of said first portion of said intravenous access system and having a non-Luer fitting on another end;

a housing having a non-Luer open end for coupling with said other end of said adapter;

a printed circuit board movable within said housing between first and second positions; and a first contact terminal disposed inside said housing and connected to a source of electrical power, wherein said printed circuit board has a second contact terminal mounted on a rear surface thereof, said light source is mounted on a front surface of said printed circuit board, and an electronic circuit connected to said second contact terminal and to said light source;

said an optical element is attached to said front surface of said printed circuit board and optically coupled to said light source;

said first and second contact terminals are not in contact when said printed circuit board is at said first position and are in contact when said printed circuit board is at said second position; and said light source emits light comprising wavelengths in a range from 390 to 492 nm when said first and second contact terminals are in contact and said electronic circuit electrically connects said second contact terminal of said printed circuit board to said light source.

10. The system as recited in claim 9, wherein said light source is a semiconductor diode.

11. The system as recited in claim 10, wherein said optical element is a lens.

12. The system as recited in claim 9, wherein said source of electrical power comprises a rechargeable battery, further comprising a photovoltaic cell electrically coupled to said rechargeable battery.

13. The system as recited in claim 9, wherein said electronic circuit is capable of cutting off the supply of power to said light source at a predetermined time subsequent to activation.

14. The system as recited in claim 9, wherein said electronic circuit is capable of controlling said light source to produce chopping-mode illumination.

15. The system as recited in claim 9, wherein said optical element comprises an outer periphery having an annular groove.

16. The system as recited in claim 9, wherein said optical element comprises a compound parabolic concentrator lens.

* * * * *